(12) United States Patent
Lorenzo et al.

(10) Patent No.: US 9,855,050 B2
(45) Date of Patent: Jan. 2, 2018

(54) VASCULATURE OCCLUSION DEVICE DETACHMENT SYSTEM WITH TAPERED COREWIRE AND SINGLE LOOP FUSE DETACHMENT

(71) Applicant: DePuy Synthes Products, LLC, Raynham, MA (US)

(72) Inventors: Juan A. Lorenzo, Davie, FL (US); Robert Slazas, Pinecrest, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 323 days.

(21) Appl. No.: 14/491,145

(22) Filed: Sep. 19, 2014

(65) Prior Publication Data

US 2016/0081694 A1    Mar. 24, 2016

(51) Int. Cl.
*A61B 17/12*    (2006.01)
*A61B 17/00*    (2006.01)

(52) U.S. Cl.
CPC .... *A61B 17/12109* (2013.01); *A61B 17/1214* (2013.01); *A61B 17/12022* (2013.01);
(Continued)

(58) Field of Classification Search
CPC ........ A61B 17/12022; A61B 17/12113; A61B 17/12109; A61B 17/1214;
(Continued)

(56) References Cited

U.S. PATENT DOCUMENTS 5,522,836 A * 6/1996 Palermo ........... A61B 17/12022
606/108

5,669,905 A    9/1997 Scheldrup et al.
(Continued)

FOREIGN PATENT DOCUMENTS

CN    203591293    5/2014
EP    1806105    7/2007
(Continued)

OTHER PUBLICATIONS

"Electrical Resitivity and Conductivity"—Wikipedia. Revision of Jul. 20, 2014. Accessed on Wikipedia on Sep. 15, 2016 at https://en.wikipedia.org/w/index.php?title=Electrical_resistivity_and_conductivity&diff=617665297&oldid=614492869.*
(Continued)

*Primary Examiner* — Shaun L David
(74) *Attorney, Agent, or Firm* — Cohen & Hildebrand, PLLC (57) ABSTRACT

A vasculature occlusion device detachment system including a heating fuse element made of a material that melts when a current is applied that exceeds a predetermined maximum current threshold. An electrically conductive corewire connected proximate its distal end directly to the heating fuse element at a first electrical connection joint, while a separate insulated electrically conductive wire is electrically connected directly to the heating fuse element at a second electrical connection joint. An inner insulation sleeve placed over a distal section of the corewire covers the first electrical connection joint and is disposed between the insulated electrically conductive wire and the electrically conductive corewire. An outer insulation sleeve is disposed over a distal section of an assembly including the insulated electrically conductive wire, the inner insulation sleeve and the electrically conductive corewire. The outer insulation sleeve covers the second electrical connection joint.

16 Claims, 4 Drawing Sheets

(52) U.S. Cl.
CPC ... *A61B 17/12113* (2013.01); *A61B 17/12154* (2013.01); *A61B 2017/00929* (2013.01); *A61B 2017/1209* (2013.01); *A61B 2017/12068* (2013.01)

(58) Field of Classification Search
CPC ...... A61B 17/12154; A61B 2017/1205; A61B 2017/1209; A61B 2017/12063
See application file for complete search history.

(56) References Cited

U.S. PATENT DOCUMENTS

| | | | |
|---|---|---|---|
| 5,725,534 | A | 3/1998 | Rasmussen |
| 5,853,418 | A | 12/1998 | Ken et al. |
| 6,013,084 | A | 1/2000 | Ken et al. |
| 6,063,100 | A | 5/2000 | Diaz et al. |
| 6,179,857 | B1 | 1/2001 | Diaz et al. |
| 6,193,728 | B1 | 2/2001 | Ken et al. |
| 6,280,457 | B1 | 8/2001 | Wallace et al. |
| 6,425,914 | B1 | 7/2002 | Wallace et al. |
| 6,458,127 | B1 | 10/2002 | Truckai et al. |
| 6,478,773 | B1 | 11/2002 | Gandhi et al. |
| 6,743,236 | B2 | 6/2004 | Barry et al. |
| 6,866,677 | B2 | 3/2005 | Douk et al. |
| 6,953,473 | B2 | 10/2005 | Porter |
| 6,966,892 | B2 | 11/2005 | Gandhi et al. |
| 7,255,707 | B2 | 8/2007 | Ramzipoor et al. |
| 7,331,973 | B2 | 2/2008 | Gesswein et al. |
| 7,582,101 | B2 | 9/2009 | Jones et al. |
| 7,651,513 | B2 | 1/2010 | Teoh et al. |
| 7,722,637 | B2 | 5/2010 | Barry et al. |
| 7,740,637 | B2 | 6/2010 | Gandhi et al. |
| 8,100,918 | B2 | 1/2012 | Gandhi et al. |
| RE43,311 | E | 4/2012 | Wallace et al. |
| 8,182,506 | B2 | 5/2012 | Fitz et al. |
| 8,273,116 | B2 | 9/2012 | Licata et al. |
| 8,298,256 | B2 | 10/2012 | Gandhi et al. |
| 8,328,860 | B2 | 12/2012 | Strauss et al. |
| 2004/0002732 | A1 | 1/2004 | Teoh et al. |
| 2004/0034363 | A1 | 2/2004 | Wilson et al. |
| 2004/0220563 | A1 | 11/2004 | Eder |
| 2005/0149108 | A1 | 7/2005 | Cox |
| 2005/0165439 | A1 | 7/2005 | Weber et al. |
| 2006/0135986 | A1 | 6/2006 | Wallace et al. |
| 2007/0112375 | A1 | 5/2007 | Aganon et al. |
| 2008/0228215 | A1 | 9/2008 | Strauss et al. |
| 2009/0177261 | A1 | 7/2009 | Teoh et al. |
| 2010/0030200 | A1 | 2/2010 | Strauss et al. |
| 2010/0063572 | A1 | 3/2010 | Teoh et al. |
| 2010/0106162 | A1 | 4/2010 | Jaeger et al. |
| 2010/0234872 | A1 | 9/2010 | Guo |
| 2011/0301686 | A1 | 12/2011 | Bowman et al. |
| 2012/0209310 | A1 | 8/2012 | Chen et al. |
| 2012/0330349 | A1 | 12/2012 | Jones et al. |
| 2013/0138136 | A1 | 5/2013 | Beckham et al. |
| 2013/0197547 | A1 | 8/2013 | Fukuoka et al. |
| 2014/0277092 | A1* | 9/2014 | Teoh ............... A61B 17/1214 606/200 |
| 2014/0277093 | A1 | 9/2014 | Guo et al. |
| 2015/0335333 | A1 | 11/2015 | Jones et al. |

FOREIGN PATENT DOCUMENTS

| | | |
|---|---|---|
| EP | 2644129 | 10/2013 |
| EP | 2644130 | 10/2013 |

OTHER PUBLICATIONS

Co-pending, co-owned, U.S. Appl. No. 14/491,109, filed Sep. 19, 2014.
European Search Report for related counterpart EP Application No. 15185745.5, dated Jan. 25, 2016 (8 pages).
European Search Report for counterpart EP Application No. 15185808, dated Feb. f, 2016 (9 pages).
"Electrical Resistivity and Conductivity"—Wikipedia. Revision of Jul. 20, 2014. Accessed on Wikipedia on Sep. 15, 2016 at https://en.wikipedia.org/w/index.php?title=Electrical_resistivity_and_conductivity&diff=617665297&oldid=614492869.

* cited by examiner

VASCULATURE OCCLUSION DEVICE DETACHMENT SYSTEM WITH TAPERED COREWIRE AND SINGLE LOOP FUSE DETACHMENT

BACKGROUND OF THE INVENTION

Field of the Invention

The present invention relates to vasculature occlusive devices (e.g., embolic coils) for implantation within a blood vessel of a body. In particular, the present invention relates to an improved heating detachment system for an embolic coil delivery system in the treatment of blood vessel disorders.

Description of Related Art

Vascular disorders and defects such as aneurysms and other arterio-venous malformations are especially difficult to treat when located near critical tissues or where ready access to malformation is not available. Both difficulty factors apply especially to cranial aneurysms. Due to the sensitive brain tissue surrounding cranial blood vessels and the restricted access, it is very challenging and often risky to surgically treat defects of the cranial vasculature.

Alternative treatments include vasculature occlusion devices, such as embolic coils, deployed using catheter delivery systems. In such systems used to treat cranial aneurysms, the distal end of an embolic coil delivery catheter is inserted into non-cranial vasculature of a patient, typically through a femoral artery in the groin, and guided to a predetermined delivery site within the cranium.

Multiple embolic coils of various lengths, generally approximately 1 cm to as long as approximately 100 cm, and preselected stiffness often are packed sequentially within a cranial aneurysm to limit blood flow therein and to encourage embolism formation. Typically, physicians first utilize stiffer coils to establish a framework within the aneurysm and then select more flexible coils to fill spaces within the framework. Ideally, each coil conforms both to the aneurysm and to previously implanted coils. Each successive coil is selected individually based on factors including stiffness, length, and preformed shape which the coil will tend to assume after delivery.

During implantation, the physician manipulates each embolic coil until it is in a satisfactory position, as seen by an imaging technique such as fluoroscopic visualization, before detaching the coil from the delivery system. It is beneficial for both ends of each coil to remain positioned within the aneurysm after delivery; otherwise, a length of coil protruding into the main lumen of the blood vessel invites undesired clotting external to the aneurysm. After each successive coil is detached, the next coil is subject to an increasing risk of becoming entangled in the growing mass of coils, thereby restricting the depth of insertion for that coil into the aneurysm.

Difficulties may arise due to stretching of the embolic coils during repositioning or attempted retrieval of the coils, especially if the coil becomes entangled and complete insertion of the coil into the aneurysm is not accomplished. If pulling forces applied to a coil exceed its elastic limit, the coil will not return to its original shape. A stretched coil exhibits diminished pushability or retractability, and becomes more difficult to manipulate into an optimal position or to be removed. Moreover, a stretched coil occupies less volume than an unstretched coil, which increases the number of coils needed to sufficiently pack the aneurysm to encourage formation of a robust embolus positioned wholly within the aneurysm. To avoid such problems stretch resistance devices are used, such as that disclosed in U.S. Pat. No. 5,853,418, herein incorporated by reference in its entirety, having a primary coil and an elongated stretch-resisting member fixedly attached to the primary cod in at least two locations.

In order to deliver the vaso-occlusive coils to a desired site, e.g., an aneurysm, in the vasculature, it is well-known to first position a relatively small profile, delivery catheter or micro-catheter at the targeted site using fluoroscopy, ultrasound, or other method of steerable navigation. A delivery or "pusher" wire is then passed through a proximal end of the catheter lumen, until a vaso-occlusive coil coupled to a distal end of the pusher wire is extended out of the distal end opening of the catheter and into the blood vessel at the targeted site. The vaso-occlusive device is then released or detached from the end pusher wire, and the pusher wire is withdrawn in a proximal direction back through the catheter. Depending on the particular needs of the patient, another occlusive device may then be pushed through the catheter and released at the same site in a similar manner.

Several conventional methods are used to detach the wire from the embolic coil once it has been properly positioned at the targeted site in the blood vessel using a delivery catheter. One known way to release a vaso-occlusive coil from the end of the pusher wire is through the use of an electrolytically severable junction, which is an exposed section or detachment zone located along a distal end portion of the pusher wire. The detachment zone is typically made of stainless steel and is located just proximal of the vase-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

One disadvantage of occlusive devices that are deployed using electrolytic detachment is that the electrolytic process requires a certain amount of time to elapse to effectuate release of the occlusive element. This time lag is also disadvantageous for occlusive delivery devices that utilize thermal detachment such as that described in U.S. Pat. No. 6,966,892, which is herein incorporated by reference in its entirety.

Another conventional detachment technique during delivery of a vase-occlusive device involves the use of fluid pressure (e.g., hydraulic detachment) to release an embolic coil once it is properly positioned, as described in U.S. Pat. Nos. 6,063,100 and 6,179,857, each of which is herein incorporated by reference in their entirety.

The main problems associated with current detachment schemes are reliability of detachment, speed of detachment, convenience of detaching mechanism (e.g., hydraulic detachment requires a high pressure syringe, while electrolytic detachment requires a battery operated box), and length/stiffness of the distal section.

It is therefore desirable to develop an improved heating detachment system for a vaso-occlusive device (e.g., an embolic coil device) that solves the aforementioned problems associated with conventional devices.

SUMMARY OF THE INVENTION

An aspect of the present invention relates to an improved heating detachment system for delivery of a vaso-occlusive device that is simpler, more reliable, quicker, more convenient and having a reduced length rigid distal section than that of conventional mechanical detachment systems.

Another aspect of the present invention is directed to an improved detachment system for delivery of a vaso-occlusive device that optimizes distal flexibility, placement at a desired treatment site and detachment characteristics.

Still another aspect of the present invention relates to a vasculature occlusion device detachment system including a heating fuse element having a predetermined resistivity, a first terminating end and an opposite second terminating end. The heating fuse element is made of a material that melts when a current is applied that exceeds a predetermined maximum current threshold. The system further includes an electrically conductive corewire electrically connected proximate its distal end directly to the first terminating end of the heating fuse element at a first electrical connection joint. An insulated electrically conductive wire separate from the electrically conductive corewire is electrically connected directly to the second terminating end of the heating fuse element at a second electrical connection joint. An inner insulation sleeve made from an electrical non-conductive material is placed over a distal section of the corewire and covers the first electrical connection joint. The inner insulation sleeve is disposed between the insulated electrically conductive wire and the electrically conductive corewire. An outer insulation sleeve made from an electrical non-conductive material is disposed over a distal section of an assembly including the insulated electrically conductive wire, the inner insulation sleeve and the electrically conductive corewire. The outer insulation sleeve covers the second electrical connection joint.

Yet another aspect of the present invention is directed to a method of using the vasculature occlusion device detachment system in the preceding paragraph. The first terminating end of the heating fuse element is electrically connected directly to the electrically conductive corewire proximate its distal end at the first electrical connection joint. Next, the inner insulation sleeve is positioned over a distal section of the electrically conductive corewire and covering the first electrical connection joint. The second terminating end of the heating fuse element is threaded through the loop of the vasculature occlusion device. A second electrical connection joint is formed by electrically connecting the second terminating end of the heating fuse element to the insulated electrically conductive wire at the second electrical connection joint. The outer insulation sleeve is positioned over a distal section of the assembly and covering the second electrical connection joint.

BRIEF DESCRIPTION OF THE DRAWING

The foregoing and other features of the present invention will be more readily apparent from the following detailed description and drawings of illustrative of the invention wherein like reference numbers refer to similar elements throughout the several views and in which.

DETAILED DESCRIPTION OF THE INVENTION

The terms "proximal"/"proximally" and "distal"/"distally" refer to a direction closer to or away from, respectively, an operator (e.g., surgeon, physician, nurse, technician, etc.) who would insert the medical device into the patient, with the tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

By way of illustrative example only, the present inventive heating detachment system is utilized for delivery of an embolic component, e.g., embolic helical coil. It is, however, intended and within the scope of the present invention to use the present inventive heating detachment system with any type of vaso-occlusive device.

Figure 1A:
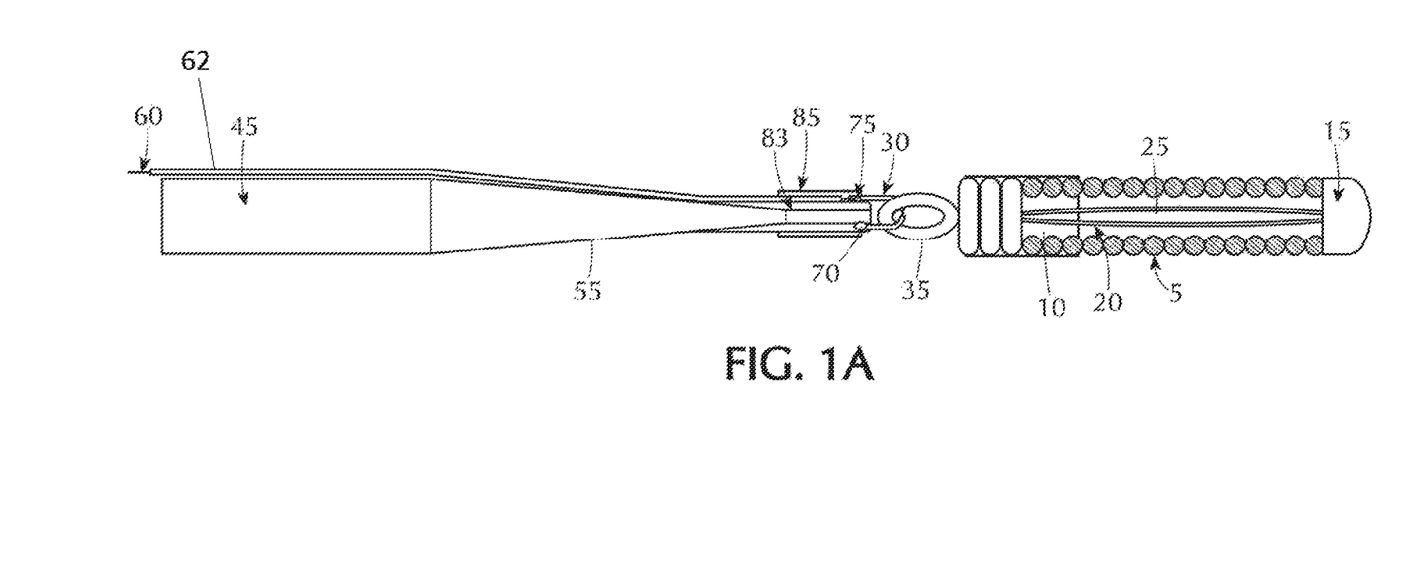
FIG. 1A is a side view of the present inventive fuse heating detachment system for an embolic coil, with a cross-sectional portion of the embolic coil showing the interior thereof.

FIG. 1A is a side view of an exemplary fuse heating detachment system in accordance with the present invention for delivery of a vaso-occlusive device, typically a helical embolic coil 5 formed by a series of loops/windings defining a coil lumen 25. The present inventive detachment system is not limited to embolic coils, but instead is equally suited for any type or shape vaso-occlusive device. Embolic coil 5 has a proximal coil junction 10 located at its proximal end. Proximal coil junction 10 is a joint, preferably made out of at least one of an adhesive, an epoxy and/or a polymer. Most preferably, the joint made of adhesive, epoxy and/or polymer is of relatively low strength and/or relatively low durometer. That is, the relatively low strength of the epoxy/ adhesive, or the relatively low durometer of the polymer used to fill that junction (which is related to its tear-out strength) is preferably less than the buckling strength of a delivery catheter used to implant the vaso-occlusive device in a blood vessel. A loop, ring or eyelet 35 extends in a proximal direction from the proximal coil junction 10 of the embolic coil 5. Preferably, only a single loop, ring or eyelet is provided on the embolic coil. Opposite its proximal end, a distal end of the embolic coil 5 is closed off by a distal bead 15. One or more stretch resistant (SR) members 20, e.g., suture filaments, disposed in the coil lumen 25 provide stretch resistance when excessive pulling forces are applied to the embolic coil 5 during implantation in a patient. Preferably, each stretch resistant member 20 extends longitudinally the entire length of the coil lumen 25 secured at its respective ends by the proximal coil junction 10 and distal bead 15 to minimize excessive elongation.

Figure 1B:
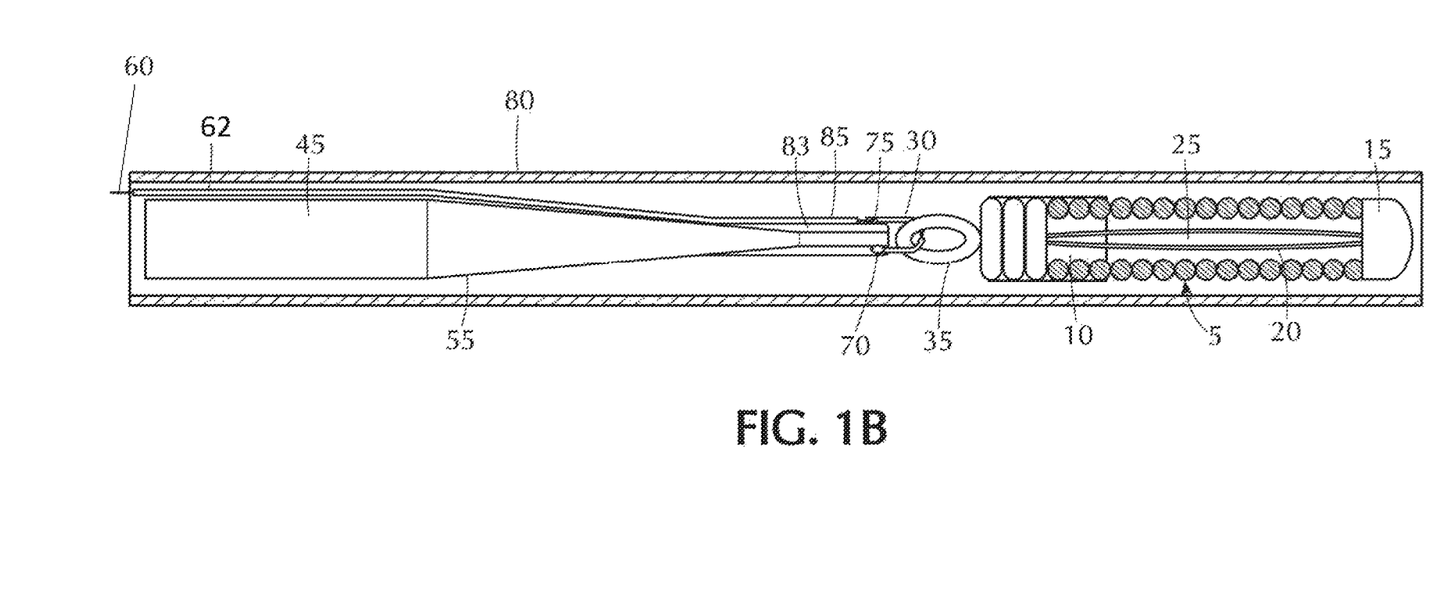
FIG. 1B is a side view of the delivery catheter with the present inventive fuse heating detachment system for an embolic coil assembled therein.

Referring to FIG. 1B, using a corewire or pusher, embolic coil 5 is advanced via a delivery catheter 80 to a target site in the body (e.g., within the blood vessel). In contrast to conventional pusher members having a central lumen, there is no central lumen defined longitudinally through the corewire of the present invention. Corewire 45 has a stiffer proximal section proximate its proximal end compared to its more flexible distal section proximate its distal end. As is illustrated in FIG. 1B, flexibility of the corewire 45 needed to advance the delivery system through distal tortuosity may be achieved by grinding tapers over its distal section, wherein the length and/or number of tapers determines the flexibility of the distal section. Thus, the length and/or number of tapers shown in the drawings are merely for illustrative purposes only and may be adapted, as desired. The corewire is made from any biocompatible electrically conductive material such as stainless steel or Nitonal. Corewire 45 may be made either as an integrated single piece construction throughout or, alternatively, as a two-piece construction secured, attached, connected or mounted together. For instance, the proximal section of the corewire may be a first material (e.g., stainless steel), while the distal section connected to the proximal section may be made of a second material (e.g., Nitonal) different than the first material. A non-conductive coating (e.g., insulation sleeve) 55 is disposed about the exterior of the corewire 45. Attached, secured, connected or otherwise mounted to its outer surface and extending preferably the length of the corewire 45 is a separate electrically conductive wire 60 insulated by an outer casing 62.

Figure 2A:
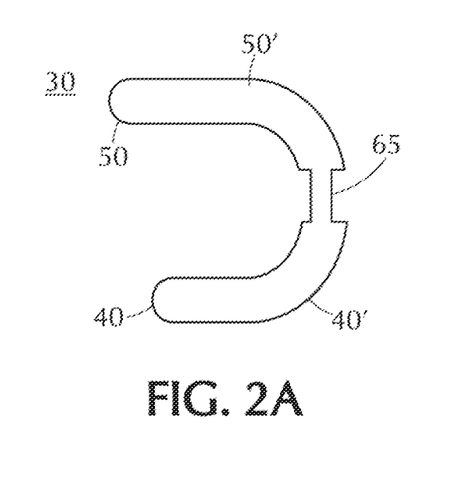
FIG. 2A is an enlarged top view of the heating fuse element with reduced localized cross-section, in a closed state prior to activation and application of a current.

A heating fuse element 30 having a given resistivity such as an electrical conductive wire or electrical conductive strip is preferably configured as a segment having two terminating ends. Typically, heating fuse element 30 is substantially U-shaped or hemispherical. Any other shape is contemplated and within the intended scope of the present invention so long as the heating fuse element 30 is configured as a segment having two terminating ends. Preferably, heating fuse element 30 has a failure section 65 substantially midway between its terminating ends. Failure section 65 is a mechanically induced deformation and/or reduced diameter (e.g., thinner) cross-section to further increase the localized electrical resistance in this section of the heating fuse element thereby narrowing or targeting the location in which the heating fuse element melts and/or severs.

Figure 3:
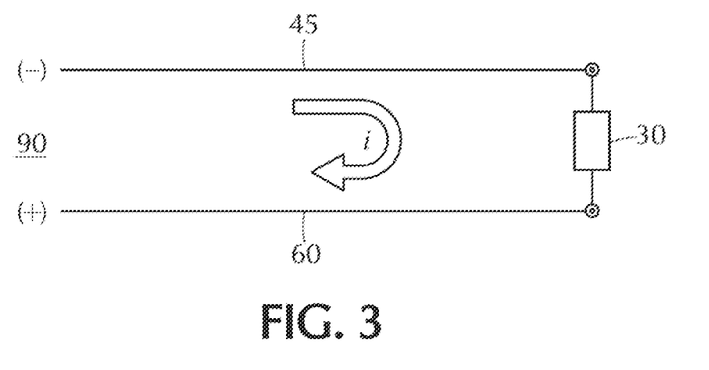
FIG. 3 is a schematic electric circuit diagram illustrating a closed loop formed by the power supply, electrically conductive corewire, the insulated electrically conductive wire and the heating fuse element.

One terminating end 40 of the heating fuse element 30 is electrically connected directly to the distal end of the corewire 45 forming a first electrical connection joint 70. An inner insulation sleeve 83 made of an electrically non-conductive material is placed over a distal section of the corewire disposed between the insulation sleeve 55 and outer casing 62 of the electrically conductive wire 60. The inner insulation sleeve 83 protects the first electrical connection joint 70 while also preventing an electrical connection between the second terminating end 50 of the heating fuse element 30 and the corewire 45. The second terminating end 50 of the heating fuse element 30 is threaded through the loop 35 of the embolic coil 5. An electrical circuit is completed or closed by electrically connecting the second terminating end 50 of the heating fuse element 30 directly to a distal end of the electrical wire 60 stripped of its outer casing 62 forming a second electrical connection joint 75. An outer insulation sleeve 85, also made of an electrically non-conductive material, is placed over at least a portion of the electrically conductive wire 60 insulated by the outer casing 62, the inner insulation sleeve 83 and the corewire 45. The outer insulation sleeve 85 secures the second electrical connection joint 75 to the outer casing 62 of the electrically conductive wire 60 while protecting the second electrical connection joint 75 itself. Either the same or different electrically non-conductive materials may be used for the inner and outer insulation sleeves 83, 85. In the electrical circuit schematic shown in FIG. 3, a power supply 90 (e.g., a battery) is connected across the conductors (i.e., proximal ends of corewire 45 and electrically conductive wire 60) producing a current across the resistive heating fuse element 30 thereby increasing the electrical resistance therein. Each of the first and second electrical connection joints 70, 75 may be established via solder, welding, conductive epoxy or any other electrical joint connection.

Figure 2B:
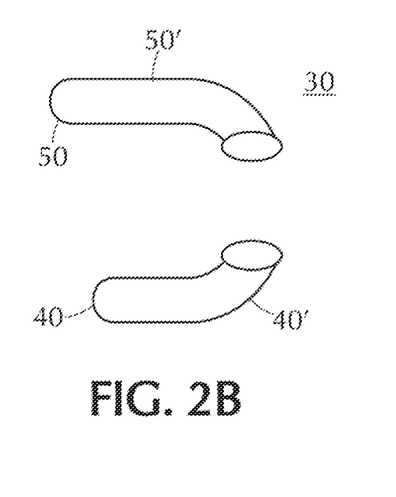
FIG. 2B is an enlarged top view of the heating fuse element of FIG. 2A, in at open state, after activation of an applied current.

In operation, the first terminating end 40 of the heating fuse element 30 is electrically connected to the corewire 45 proximate its distal end thereby forming the first electrical joint 70. Inner insulation sleeve 83 is positioned over a distal section of the electrically conductive corewire 45 while also covering the first electrical connection joint 70. The second terminating end of 50 of the heating fuse element 30 is then threaded through the loop 35 of the embolic coil 5. Once threaded through the loop 35, the second terminating end 50 of the heating fuse element 30 is electrically connected to the electrically conductive wire 60 at the second electrical connection joint 75. Next, the outer insulation sleeve 85 is positioned over a distal section of the assembly (including the electrically conductive wire 60 insulated by the outer casing 62, the inner insulation sleeve 83 and the electrically conductive corewire 45) and is also positioned to cover the second electrical connection joint 75. Now that the delivery device has been assembled, using the electrically conductive corewire 45 the vasculature occlusion device 5 is advanced via the delivery catheter 80 to a target site in a human body. Once the embolic coil 5 has been properly positioned at a desired treatment site within the blood vessel, electrical activation of the heating element 30 by the power source (e.g., a battery) 90 increases the electrical resistance therein. Due to its design, the resistance is greatest in the failure section 65 of the heating fuse element 30. An increase in the resistance in the failure section 65 beyond the predetermined threshold tolerance of the material causes the failure section 65 of the heating fuse element 30 to melt and thus sever thereby releasing the embolic coil 5 secured therein. Thereafter, the delivery catheter 80, corewire 45, electrically conductive wire 60 insulated by the outer casing 62 and heating element 30 are withdrawn from the human body by pulling in a proximal direction leaving in place the embolic coil 5 within the blood vessel at its desired treatment site.

The present inventive detachment system advantageously minimizes the length (as measured from approximately its midsection to one of its terminating ends) of the heating fuse element 30. For example, with this alternative embodiment such length of the heating fuse element may be reduced to a range between approximately 1.0 mm to approximate 3.0 mm, preferably approximately 2 mm.

Additional design factors or considerations are contemplated other than that of maximizing heat transfer to the coil securing suture. On the one hand, the heating fuse element 30 is desirably sufficiently long (as measured in an axial direction) to produce sufficient resistance when the embolic coil 5 is implanted. While on the other hand, the length of the heating element 30 is sufficiently short to minimize micro-catheter kick back (i.e., push back out of aneurysm). A shorter length heating element also optimizes the flexibility of the distal end of the coil delivery system desirable during delivery of the vaso-occlusive device to the target site in the human body.

In accordance with the present invention, the corewire serves as one of the electrical conductors and the insulated electrically conductive wire as the other electrical conductor in forming a closed loop electrical path along with the power supply and heating fuse element. Preferably, the corewire also serves the dual function of advancing the vaso-occlusive device in the delivery catheter. In response to current provided by the power supply a sufficient resistance is produced in the heating fuse element that melts and/or severs at least a section thereof (e.g., the failure section 65) thereby releasing the embolic coil at a target site within the body.

The present invention has been shown and described for delivery and detachment of an embolic coil. Other vaso-occlusive devices are contemplated and within the scope of the present invention.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A detachment system comprising:
    a heating fuse element having a predetermined resistivity; the heating fuse element having a first terminating end and an opposite second terminating end; the heating fuse element being made of a material that melts or severs when an applied current exceeds a predetermined maximum current threshold;
    an electrically conductive corewire having a proximal end and an opposite distal end; the electrically conductive corewire being electrically connected proximate the distal end of the electrically conductive corewire directly to the first terminating end of the heating fuse element at a first electrical connection joint; and
    an electrically conductive wire insulated by an outer casing, the electrically conductive wire being separate from the electrically conductive corewire; the electrically conductive wire having a proximal end and an opposite distal end; the distal end of the electrically conductive wire being electrically connected directly to the second terminating end of the heating fuse element at a second electrical connection joint;
    an inner insulation sleeve made from an electrical non-conductive material; the inner insulation sleeve is disposed over a distal section of the corewire and covers the first electrical connection joint; the inner insulation sleeve is disposed between the outer casing of the electrically conductive wire and the electrically conductive corewire; and
    an outer insulation sleeve made from an electrical non-conductive material; the outer insulation sleeve is disposed over a distal section of an assembly including the electrically conductive wire insulated by the outer casing, the inner insulation sleeve and the electrically conductive corewire; the outer insulation sleeve covers the second electrical connection joint.

2. The system in accordance with claim 1, further comprising a power source electrically connected to the respective proximal ends of the electrically conductive corewire and the electrically conductive wire.

3. The system in accordance with claim 1, wherein the heating fuse element is a conductive wire or a conductive strip.

4. The system in accordance with claim 1, wherein the electrically conductive corewire is tapered from the proximal end of the electrically conductive corewire towards the distal end of the electrically conductive corewire.

5. The system in accordance with claim 1, further comprising a vasculature occlusion device having a proximal end and an opposite distal end; a loop protrudes in a proximal direction from the proximal end of the vasculature occlusion device; the heating fuse element being threaded through the loop.

6. The system in accordance with claim 1, wherein the electrically conductive corewire does not have a lumen defined therein.

7. The system in accordance with claim 1, wherein the heating fuse element is U-shaped or hemispherical in shape.

8. The system in accordance with claim 1, wherein a length of the heating fuse element measured from approximately the midsection of the heating fuse element to one of the terminating ends of the heating fuse element is between approximately 1 mm and approximately 3 mm.

9. The system in accordance with claim 1, wherein the heating fuse element has a failure section approximately midway between the first terminating end and the second terminating end; the failure section of the heating fuse element having a mechanically induced deformation and/or reduced diameter cross-section to induce failure therein.

10. The system in accordance with claim 1, wherein the electrically conductive corewire has a two-piece construction comprising a stiffer proximal section proximate the proximal end of the electrically conductive corewire secured to a more flexible distal section proximate the distal end of the electrically conductive corewire; the stiffer proximal section of the electrically conductive corewire being made of a first material and the more flexible distal section of the electrically conductive corewire being made of a second material different than the first material.

11. A method of using a detachment system including: a heating fuse element having a predetermined resistivity; the heating fuse element having a first terminating end and an opposite second terminating end; the heating fuse element being made of a material that melts or severs when an applied current exceeds a predetermined maximum current threshold; an electrically conductive corewire having a proximal end and an opposite distal end; the electrically conductive corewire being electrically connected proximate the distal end of the electrically conductive corewire directly to the first terminating end of the heating fuse element at a first electrical connection joint; and an electrically conductive wire insulated by an outer casting, the electrically conductive wire being separate from the electrically conductive corewire; the electrically conductive wire having a proximal end and an opposite distal end; the distal end of the electrically conductive wire being electrically connected directly to the second terminating end of the heating fuse element at a second electrical connection joint; an inner insulation sleeve made from an electrical non-conductive material; the inner insulation sleeve is disposed over a distal section of the corewire and covers the first electrical connection joint; the inner insulation sleeve is disposed between the outer casing of the electrically conductive wire and the electrically conductive corewire; an outer insulation sleeve made from an electrical non-conductive material; the outer insulation sleeve is disposed over a distal section of an assembly including the electrically conductive wire insulated by the outer casing, the inner insulation sleeve and the electrically conductive corewire; the outer insulation sleeve covers the second electrical connection joint; and a vasculature occlusion device having a proximal end and an opposite distal end; a loop protrudes in a proximal direction from the proximal end of the vasculature occlusion device; the heating fuse element being threaded through the loop, the method comprising the steps of:

electrically connecting the first terminating end of the heating fuse element to the electrically conductive corewire proximate the distal end of the electrically conductive corewire at the first electrical connection joint;

positioning the inner insulation sleeve over a distal section of the electrically conductive corewire and covering the first electrical connection joint;

threading the second terminating end of the heating fuse element through the loop of the vasculature occlusion device;

electrically connecting the second terminating end of the heating fuse element to the electrically conductive wire at the second electrical connection joint; and     positioning the outer insulation sleeve over a distal section of the assembly and covering the second electrical connection joint.

12. The method in accordance with claim 11, further comprising the steps of:

advancing the vasculature occlusion device via a delivery catheter through a human body using the electrically conductive corewire;

positioning the vasculature occlusion device at a target site in the human body;

applying an electrical current powered by a power source to the electrically conductive corewire and the electrically conductive wire beyond the predetermined maximum current threshold of a portion of the heating fuse element;

as a result of the applied electrical current, increasing an electrical resistance of the heating fuse element;

generating sufficient heat due to the increased electrical resistance to melt and sever the portion of the heating fuse element thereby releasing the vasculature occlusive device from the heating fuse element; and     withdrawing from the human body by pulling in a proximal direction the delivery catheter, the heating fuse element and the electrically conductive corewire, while leaving at the target site in the human body the vasculature occlusive device.

13. The method in accordance with claim 11, wherein the heating fuse element is U-shaped or hemispherical in shape.

14. The method in accordance with claim 11, wherein a length of the heating fuse element measured from the midsection of the heating fuse element to one of the terminating ends of the heating fuse element is between approximately 1 mm and approximately 3 mm.

15. The method in accordance with claim 11, wherein the heating fuse element has a failure section approximately midway between the first terminating end and the second terminating end; the failure section of the heating fuse element having a mechanically induced deformation and/or reduced diameter cross-section to induce failure therein.

16. The method in accordance with claim 11, wherein the electrically conductive corewire has a two-piece construction comprising a stiffer proximal section proximate the proximal end of the electrically conductive corewire secured to a more flexible distal section proximate the distal end of the electrically conductive corewire; the stiffer proximal section of the electrically conductive corewire being made of a first material and the more flexible distal section of the electrically conductive corewire being made of a second material different than the first material.

\* \* \* \* \*